United States Patent [19]

Barr

[11] Patent Number: Plant 6,616

[45] Date of Patent: Feb. 21, 1989

[54] *NERIUM OLEANDER* 'HINES HARDY'

[75] Inventor: William C. Barr, Rosenberg, Tex.

[73] Assignee: Weyerhaeuser Company, Tacoma, Wash.

[21] Appl. No.: 75,011

[22] Filed: Jul. 17, 1987

[51] Int. Cl.[4] ..... A01H 5/00

[52] U.S. Cl. ..... Plt./54

[58] Field of Search ..... Plt./54

*Primary Examiner*—Robert E. Bagwill

[57] ABSTRACT

A new and distinct variety of *Nerium oleander* L. generally similar in appearance to Nerium "Hardy Red" cultivar but having outstanding cold tolerance enabling cultivation in environments having USDA Zone 7 (0°-10° F.) winter conditions.

2 Drawing Sheets

SUMMARY OF THE INVENTION

The present invention relates to a new and distinct plant cultivar of *Nerium oleander* L. commonly known as "Oleander" in the Apocynaceae family.

This new Nerium cultivar was discovered during the late winter (February-March) of 1982 as a plant within a 12 m wide median strip planting of Nerium along U.S. Highway 90 Alt., approximately 1.6 km east of Texas Highway 6, in the city of Sugar Land, Tex. A relatively severe winter had caused browning and other obvious cold damage to all of the other Nerium plants in the planting. The observed plant was outstanding because it had good color and seemed unaffected by the cold weather. It appeared that all of the Nerium plants in the planting were of the same variety with the observed plant being a cold tolerant sport and new variety. The variety of the plants originally in the planting cannot now be ascertained since the entire planting, including the mother plant of this new variety, was destroyed by roadside construction during the summer of 1983. Prior to that time cuttings were obtained from the cold tolerant plant. These have been propagated and appear to be a distinct new cultivar of Nerium.

*Nerium oleander* 'Hines Hardy' has many desirable and distinctive characteristics which render it unique from any other *Nerium oleander* cultivar.

The unique ability of this distinct selection to withstand temperatures as low as −15° C. without damage is greater than any *Nerium oleander* cultivar that has ever been offered in the nursery trade. It appears to be sufficiently hardy for growing in USDA Zone 7 (0° to 10° F., −17.8° to −12.2° C.). Other distinct characteristics of *Nerium oleander* 'Hines Hardy' include its smaller leaf, finer texture and lighter green color compared with Nerium var. "Hardy Red".

*Nerium oleander* 'Hines Hardy' has been reproduced numerous times by asexual propagation (vegetative cuttings). Each of the progeny exhibits identical characteristics to the original mother plant establishing this selection as reproducable and true to type.

BRIEF DESCRIPTION OF THE PHOTOGRAPHS

DETAILED PLANT DESCRIPTION

After an extensive evaluation period, *Nerium oleander* 'Hines Hardy' was found distinct from any other Nerium cultivar that is presently offered or has ever been offered in the nursery trade. The following is a detailed description of the performance and appearance of *Nerium oleander* 'Hines Hardy'. Descriptions are based on not less than 15 specimens for each specified characteristic. Color determinations and comparisons are all based on the Royal Horticultural Society Colour Chart.

Overall size and growth habit:

*Size.*—The ultimate size of *Nerium oleander* 'Hines Hardy' is unknown as no specimen has yet reached full maturity. The original mother plant from which the initial cuttings were collected was approximately 2 m tall with a 3 m spread.

Figure 1:
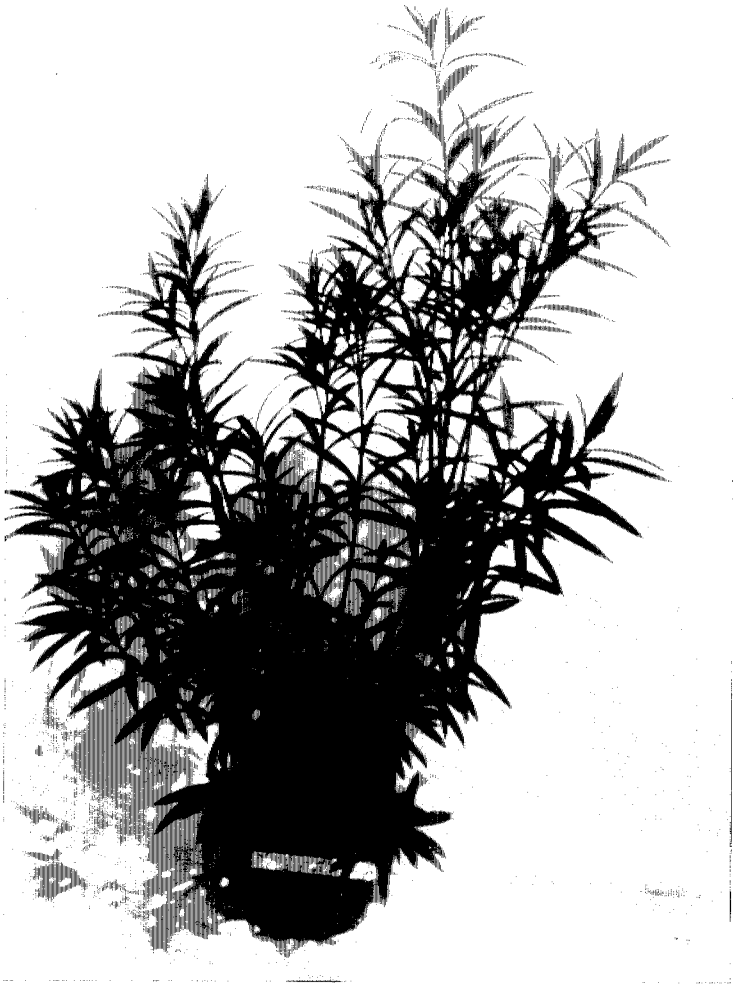
FIG. 1 shows an immature plant of the new variety approximately 2½ to 3 years after taking the cutting. The plant shown is in a #5 container and is about 1.5 m in overall height.

*Habit.*—Erect, somewhat open, bushy shrub (FIG. 1).

Foliage:

*Arrangement.*—Opposite or in whorls of 3 to 4.

Figure 2:
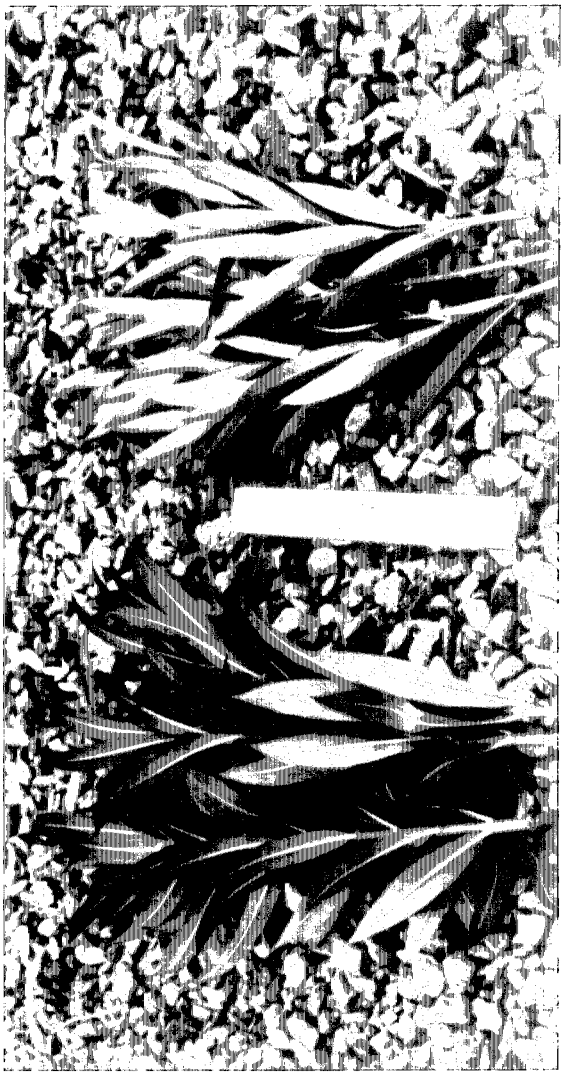
FIG. 2 shows a comparison of the foliage of the new variety, shown on the right, with that of Nerium "Hardy Red" on the left.

*Size (FIG. 2, right).*—Average leaf width — 1.7 to 2.5 cm (average of 15 count). Average leaf length from petrole to leaf tip — 11.8 cm to 15.8 cm.

*Color (FIG. 2, right).*—Upper leaf surface: R.H.S. Colour Chart Fan 3, Green Group No. 137A. Lower leaf surface: R.H.S. Colour Chart Fan 3, Yellow-green Group, No. 146B.

*Shape and form.*—Linear to lanceolate, upright. Margins — entire, apex acute, surface leathery. Texture — medium/fine.

Inflorescence: Flowers are in terminal corymbs, approximately 5 cm across. Single, short petioled, five lobed, not scented, and the corolla tube is funnel formed.

*Bloom period.*—Late spring through summer months depending upon weather conditions.

*Color.*—Medium red with a purple cast. Approaching R.H.S. Colour Chart Fan 2, Red-Purple Group No. 57B. Substantially identical to that of a non-patented Nerium variety which is sometimes identified within the nursery trade as "Hardy Red" Oleander, Nerium "Single Hardy Red", "Single Hardy Red" Oleander, or Nerium "Cardinal".

Hardiness: The most significant different characteristic of *Nerium oleander* 'Hines Hardy' is its ability to withstand cold temperatures without damage. During late December 1983 and early January 1984 temperatures dropped to −11° C. at the lowest and remained below freezing (0° C.) for approximately 17 days at the Hines Nursery site in Houston, Tex. During this freeze event, 100% of all unprotected Nerium varieties, regardless of size, including Nerium "Hardy Red" and Nerium "Little Red" (U.S. Plant Pat. No. 3,856) were destroyed (top and root killed). During this same event, the original stock plants of *Nerium oleander* 'Hines Hardy' in #5 containers did not exhibit any harmful effects either to the foliage or root systems. This freeze severely damaged and killed many other broadleaf evergreens growing at the same site including *Ligustrum japonicum* "Texanum" (USDA Zone 7), *Pittosporum tobira* (USDA Zone 8), *Ilex cornuta* "Burfordi" (USDA Zone 7), Photonia×"Fraseri" (USDA Zone 7).

In September, 1986, test plants of *Nerium oleander* 'Hines Hardy' were planted in the ground in the same vicinity as established plants of Nerium "Hardy Red" in Albuquerque, N. Mex. During February, 1987, Albuquerque, N. Mex., experienced winter low temperatures of −15° to −17° C. While all of the Nerium "Hardy Red" plants were destroyed (tops and roots), *Nerium oleander* 'Hines Hardy' only suffered minimal leaf burn. This event again confirmed that even unestablished plants of *Nerium oleander* 'Hines Hardy' are capable of withstanding lower temperatures than any other similar Nerium in the nursery trade.

DESCRIPTION OF NERIUM "HARDY RED"

Nerium "Hardy Red" was chosen as a comparison plant because of all the Nerium varieties presently grown in the nursery trade it most closely resembles *Nerium oleander* 'Hines Hardy' in appearance. *Nerium oleander* 'Hines Hardy' is a standard variety of *Nerium oleander* and has been in cultivation for over sixty years and is widely distributed throughout the nursery trade.

Descriptions and comparisons are based on an average of not less than 15 specimens for each specified characteristic. Comparisons were formulated from side-by-side evaluations of both container and field-grown specimens. Comparison plants are of the same age and have been grown in the same environment and with the exact same cultural techniques.

Mature height: 8–12 feet.

Plant habit: Erect, somewhat open, bushy shrub.

Flower color: Medium red with a purple cast, approaching R.H.S. Colour Chart Fan 2, Red Purple Group No. 57B.

Foliage size (FIG. 2 left):

*Average leaf width.*—2.0 cm to 3.0 cm (average of 15 count).

*Average leaf length.*—From petiole to leaf tip, 13.3 cm to 17.7 cm (average of 15 count).

Foliage color (FIG. 2):

*Upper leaf surface.*—R.H.S. Colour Chart Fan 3 Yellow Green Group No. 147A.

*Lower leaf surface.*—R.H.S. Colour Chart Fan 3 Yellow Green Group No. 147B.

Hardiness: USDA Zones 8–9 (10° to 30° F., −12.2° C. to −1.1° C.).

I claim:

1. A new and distinct variety of *Nerium oleander* L. substantially as shown and described, characterized by:

a. leaves slightly narrower and shorter than those of Nerium "Hardy Red" cultivar;

b. flowers essentially identical in color to Nerium "Hardy Red" cultivar; and c. having outstanding cold tolerance enabling cultivation in environments having USDA Zone 7 (0°–10° F.) winter conditions.

* * * * *

VAR. "HARDY RED"

VAR. "BILL BARR No. 3"

UNITED STATES PATENT AND TRADEMARK OFFICE

CERTIFICATE OF CORRECTION

PATENT NO. : Plant 6,616

DATED : February 21, 1989

INVENTOR(S) : William C. Barr

It is certified that error appears in the above-identified patent and that said Letters Patent is hereby corrected as shown below:

In column 4, line 1, "oleander 'Hines Hardy' " to read -- 'Hardy Red' --

Signed and Sealed this

Nineteenth Day of December, 1989

*Attest:*

JEFFREY M. SAMUELS

*Attesting Officer* *Acting Commissioner of Patents and Trademarks*